United States Patent
Ling

(10) Patent No.: US 10,702,896 B2
(45) Date of Patent: Jul. 7, 2020

(54) METHOD FOR CLEANING A METAL SURFACE OF A METAL COMPONENT OF AN INDUSTRIAL PLANT

(71) Applicant: Basell Polyolefine GmbH, Wesseling (DE)

(72) Inventor: Antonio Ling, Erftstadt (DE)

(73) Assignee: Basell Polyolefine GmbH, Wesseling (DE)

(*) Notice: Subject to any disclaimer, the term of this patent is extended or adjusted under 35 U.S.C. 154(b) by 331 days.

(21) Appl. No.: 15/868,701

(22) Filed: Jan. 11, 2018

(65) Prior Publication Data
US 2018/0207692 A1 Jul. 26, 2018

(30) Foreign Application Priority Data

Jan. 24, 2017 (EP) .................................... 17152743

(51) Int. Cl.
*B08B 9/027* (2006.01)
*C08F 10/02* (2006.01)
(Continued)

(52) U.S. Cl.
CPC ................ *B08B 9/027* (2013.01); *C07C 4/04* (2013.01); *C08F 10/02* (2013.01); *C08F 10/06* (2013.01);
(Continued)

(58) Field of Classification Search
None
See application file for complete search history.

(56) References Cited

U.S. PATENT DOCUMENTS 3,227,988 A * 1/1966 Walsh ....................... H05F 3/02
439/39
4,181,536 A * 1/1980 Keyworth ................ F28G 9/00
134/2
(Continued)

FOREIGN PATENT DOCUMENTS

WO    WO-2015197561 A1 * 12/2015 ................ C08F 2/18

OTHER PUBLICATIONS

The Extended European Search Report for EP17152743.5 dated May 19, 2017.

*Primary Examiner* — Nicole Blan

(57) ABSTRACT

A method for cleaning a metal surface of a metal component of an industrial plant is disclosed comprising measuring the electrical resistance $R_{A1}$ of a metal component over a cleaned area of the metal surface with a resistance meter, comparing the electrical resistance $R_{A1}$ measured with a pre-determined electrical resistance value $R_{DET}$, assessing whether $R_{A1}$ is greater, smaller or equal to $R_{DET}$, and repeating cleaning if the electrical resistance $R_{A1}$ measured is greater than $R_{DET}$, or terminating cleaning of the surface area of the metal component if $R_{A1}$ is smaller than or identical to $R_{DET}$.

18 Claims, 2 Drawing Sheets

(51) Int. Cl.
  *G01N 27/04* (2006.01)
  *C07C 4/04* (2006.01)
  *C23G 5/00* (2006.01)
  *G01R 1/067* (2006.01)
  *C08F 10/06* (2006.01)
  *F28G 9/00* (2006.01)
  *B08B 3/02* (2006.01)

(52) U.S. Cl.
  CPC ................. *C23G 5/00* (2013.01); *F28G 9/00* (2013.01); *G01N 27/041* (2013.01); *B08B 3/02* (2013.01); *G01N 27/04* (2013.01); *G01R 1/06788* (2013.01)

(56) References Cited

U.S. PATENT DOCUMENTS

| | | |
|---|---|---|
| 4,280,852 A | 7/1981 | Dunham et al. |
| 4,515,641 A | 5/1985 | Juenger |
| 5,396,178 A | 3/1995 | Rybarski |
| 2005/0042757 A1 | 2/2005 | Famme |
| 2005/0228151 A1* | 10/2005 | Agapiou ............... C08F 210/16 526/68 |
| 2013/0003048 A1 | 1/2013 | Caussin De Schneck et al. |

* cited by examiner

METHOD FOR CLEANING A METAL
SURFACE OF A METAL COMPONENT OF
AN INDUSTRIAL PLANT

CROSS-REFERENCE TO RELATED
APPLICATIONS

This application claims the benefit of priority to European Patent Application No. EP17152743.5, filed on Jan. 24, 2017, which is incorporated herein by reference in its entirety.

FIELD OF THE INVENTION

The present disclosure relates to a method for cleaning a metal surface of a metal component of an industrial plant. The present disclosure in particular relates to a method for cleaning metal surfaces of metal components of plants for the preparation of ethylene, propylene, polyethylene or polypropylene and to a method for cleaning metal surfaces of cracking furnaces.

BACKGROUND OF THE INVENTION

Maintenance of production plants may comprise regular cleaning of all of its components or at least some of its crucial components. During usage of equipment layers can be formed on metal surfaces thereof, e.g. by soiling, crystallization, sedimentation, chemical fouling, biological fouling, or the like. Depending on the process performed in the production plant these layers comprise, for example, coke, fouling, polymer, resins, bitumen, etc.

Cleaning can for example be accomplished by mechanical means such as high water pressure and/or the use of brushes or scrapers or by chemical means using specifically designed chemical cleaning agents.

The cleaning result is often merely assessed by visual means. However, in particular with rather complex plant designs not all parts of the equipment cleaned can be properly visually inspected. Here, it just remains to rely on the experience of the cleaning personnel gathered during earlier cleaning cycles. Still there remains a great amount of uncertainty of whether all components of an industrial plant have been sufficiently cleaned. Incomplete cleaning results may lead to additional and/or prolonged process downtime, processing delays and in turn also to increased manufacturing costs.

In those cases in which it is impossible to visually inspect cleaned surface areas the cleaning personnel is either left to omit any checking of the degree of the cleaning of such sites or to rely on experience. Moreover, different methods could be tried to determine the degree of cleaning, for example, by use of rather elaborated analytical methods.

For cleaning operations of metal surfaces of metal components of petrochemical plants. high-pressure water jets may be used. Water pressure can for example be in the range from 1,000 to 1,600 bar. Even though rather high water pressures are used, which can be combined with high water temperatures, it can still not be guaranteed that the treated metal surfaces are sufficiently clean. In some instances, even though a cleaned surface provides an immaculate surface upon visual inspection, reactor fouling caused by undetected remnants or coatings may occur at a much too early stage.

If a production plant is not regularly subjected to maintenance work, including the cleaning of its components, its efficiency may drastically decrease. And, instead of cleaning or restoration work either part of the plant or the entire plant needs to be replaced. Soiled surfaces in production plants, particular in chemical production plants may lead to lower performance in heat transfer, pressure losses, decreased streaming volume, higher leaking risks during operation, and higher operation and maintenance costs.

In US 2005/0042757 A1, a method of determining the cleanness of an apparatus is disclosed which comprises treating the interior of the apparatus with a solution comprising permanganate. Any contaminants still being present in the apparatus will react with permanganate. Non-reacted permanganate will be rinsed off with water. Subsequently, the interior of the apparatus having thus been treated with permanganate is described to be contacted with a solution comprising peroxide. If remnants are still present, hydrogen peroxide will react and be split into oxygen and water. That is, if oxygen and water are still detected, the interior of an apparatus should still contain contaminations. Only in case in which there is no detecting of hydrogen peroxide having been split into oxygen and water, it can be implied that the interior of an apparatus is sufficiently clean.

Another method allowing for determining that a piece of equipment is clean can be found in U.S. Pat. No. 5,396,178. In a first step an aqueous liquid rinse medium is caused to come into contact with a cleaned piece of equipment. The electrical conductivity of said aqueous liquid medium is determined both prior to and after rinsing. If the electrical conductivity determined after rinsing substantially equals said electrical conductivity determined prior to rinsing the claimed piece of equipment is considered to be sufficiently clean and cleaning is terminated.

Yet another process for cleaning control through measurement of electrical conductivity is disclosed in U.S. Pat. No. 4,515,641. According to this process the interior wall of a contaminated metal vessel or pipe is flooded or turbulently impacted with a strongly alkaline or strongly acidic cleaning fluid. Simultaneously the conductivity of the cleaning fluid is measured between two electrodes located in the interior of said vessel or pipe. These electrodes are to be electrically insulated and separated from each other, with at least one of said electrodes having been subjected to contamination while located in the interior of said vessel or pipe. Flooding or impacting is terminated when the measured conductivity has been substantially restored to a reference level.

US 2013/0003048 A1 discloses a fouling detection setup and a method for determining the amount of fouling of surfaces of fluid treating devices and/or internal functional components of such devices, which are exposed to the fluid and are subjected to fouling. The method includes a step of measuring the electrical conductive conductivity and/or optical transparency of the fluid at a position nearby or within the surfaces of the fluid treating devices and/or internal functional components of such devices.

U.S. Pat. No. 4,515,641 discloses a method of sensing the cleaning progress of a cleaning tool in a heat exchanger tube comprising the steps of applying a voltage between the tube and a sensor element of a tube cleaning tool being rotated in the tube, utilizing a current variation signal in a path between the sensor element and tube to produce an input signal representative of resistance to current flow as the tool is rotated for cleaning the tube, and producing an indicator output signal in response to the input signal.

The processes for checking the degree of cleaning of manufacturing equipment are still rather complex and cumbersome and may need sophisticated detecting devices. Therefore, a continuing need exists for cleaning processes which reliably furnish cleaned surfaces of components in production plants while these processes simultaneously allow to ascertain in a fast and precise manner that a sufficient degree of cleaning has been accomplished.

SUMMARY OF THE INVENTION

The present disclosure provides a method for cleaning a metal surface of a metal component of an industrial plant.

The present disclosure thus provides a method for cleaning a metal surface of a metal component of an industrial plant, comprising the steps of
a) cleaning at least one area of a metal surface of a metal component after having been put into operation for an interval,
b) optionally drying the cleaned area of the metal surface of the metal component,
c) providing a pre-determined electrical resistance value $R_{DET}$ which represents an electrical resistance indicative of a sufficiently cleaned metal surface of the metal component of the industrial plant,
d) measuring the electrical resistance $R_{A1}$ of the surface of the metal component at at least one point of the cleaned area by at least one resistance meter,
e) comparing the electrical resistance $R_{A1}$ measured according to step d) with the pre-determined electrical resistance value $R_{DET}$, and
f) repeating steps a), d) and e), and optionally b), if the electrical resistance $R_{A1}$ is greater than the pre-determined electrical resistance value $R_{DET}$, or
g) terminating cleaning of the surface area of the metal component if the electrical resistance value $R_{A1}$ is smaller than or identical to the pre-determined electrical resistance value $R_{DET}$.

In some embodiments, the metal component is a heat exchanger, container, reactor, tank, vessel, pipe, cracking furnace, tube, filter, silo truck, tank wagon or a part thereof.

In some embodiments, the industrial plant is a chemical or petrochemical plant.

In some embodiments, the measuring of the electrical resistances occurs by a resistance meter comprising at least one probing tip and another contact, which is the counter tip, and the counter tip is a punctual tip held by a magnet to a surface of the metal component of the industrial plant or to a surface of a metal part in electrical connection with the metal component of the industrial plant.

In some embodiments, the counter tip is movably installed within a counter tip holder comprising a magnet and a compression spring.

In some embodiments, the measuring of the electrical resistances occurs by a resistance meter comprising at least one sliding contact, in particular two or more sliding contacts, wherein the at least one sliding contact represents the probing tip, and another contact is the counter tip.

In some embodiments, the metal surface is the inner surface of a tube in a heat exchanger and the measuring of the electrical resistances occurs by a resistance meter comprising at least one sliding contact as probing tip and another contact as counter tip, and the at least one sliding contact can be moved to all positions of the inner surface of the tube.

In some embodiments, one or more defined surface areas are selected from the at least one area of the metal surface of the metal component having been cleaned according to step a), and optionally dried according to step b), and solely said one or more defined surface areas are subjected to process steps d) and e).

In some embodiments, the cleaning of the industrial plant or of a metal component thereof is terminated as soon as the one or more defined surface areas meet the requirement of process step g).

In some embodiments, in step d), the electrical resistance $R_{A1}$ of the metal component is measured along a continuous path or intermittently at the cleaned area of the metal surface.

In some embodiments, the electrical resistance $R_{A1}$ of the metal component cleaned according to step a), and optionally step b), is measured in step d) by
moving the probing tip over at least part of the cleaned area of the metal surface, and
having placed the counter tip on a metal surface area belonging to the cleaned metal surface of the metal component of the industrial plant after step a), and optionally step b), have been completed and after said metal surface area of the cleaned metal surface area has subsequently been subjected to at least one scraping, brushing, grinding, etching, pickling and/or polishing step, or
having placed the counter tip on a metal surface area, wherein said metal surface area is not exposed to the process run in the chemical plant and which does not belong to the cleaned metal surface of the metal component of the industrial plant after step a), and optionally step b), have been completed, and wherein said metal surface area is on said metal component of the industrial plant comprising the cleaned area of the metal surface or is on a metal component which is in electrical connection with said metal component of the industrial plant comprising the cleaned area of the metal surface.

In some embodiments, said metal surface area which is not exposed to the process run in the chemical or petrochemical plant and which does not belong to the cleaned metal surface of the metal component of the industrial plant after step a), and optionally step b), have been completed, is subjected to at least one scraping, brushing, grinding, etching, pickling and/or polishing step before the counter tip is brought in contact therewith.

In some embodiments, the method further comprising, for controlling or adjusting the initial conditions for measuring the electrical resistance of cleaned metal surfaces,
i) measuring, prior to step d), a first test electrical resistance value $R_{O1}$ on a first metal surface area belonging to the cleaned metal surface of the metal component of the industrial plant after steps a), and optionally b), have been completed and after said first metal surface area of the cleaned metal surface area has subsequently been subjected to at least one scraping, brushing, grinding, etching, pickling and/or polishing step in order to bare the metal, and
ii) commencing with step d) if the first test electrical resistance value $R_{O1}$ is identical to or below a predetermined threshold resistance value $R_{THRESHOLD}$, which is below the pre-determined electrical resistance value $R_{DET}$, by having the counter tip placed on said first metal surface area, or
iii) repeating the at least one scraping, brushing, grinding, etching, pickling and/or polishing step if the first test electrical resistance value $R_{O1}$ is above the predetermined threshold resistance value $R_{THRESHOLD}$ and commencing with steps i) and ii).

In some embodiments, the method further comprising, for controlling or adjusting the initial conditions for measuring the electrical resistance of cleaned metal surfaces,
i) measuring, prior to step d), a second test electrical resistance value Roe on a second metal surface area, wherein said second metal surface area is not exposed to the process run in the chemical plant and which does not belong to the cleaned metal surface of the metal component of the industrial plant, and wherein said second metal surface area is either on said metal component of the industrial plant comprising the cleaned area of the metal surface or is on a metal component which is in electrical connection with said metal component of the industrial plant comprising the cleaned area of the metal surface, ii) commencing with step d) if the second test electrical resistance value $R_{O2}$ is identical to or below a predetermined threshold resistance value $R_{THRESHOLD}$, which is below the pre-determined electrical resistance value $R_{DET}$, by having the counter tip placed on said second metal surface area, or iii) subjecting the second metal surface area to at least one scraping, brushing, grinding, etching, pickling and/or polishing step if the second test electrical resistance value $R_{O2}$ is above the predetermined threshold resistance value $R_{THRESHOLD}$ and commencing with steps i) and ii).

In some embodiments, the second test electrical resistance value $R_{O2}$ is measured on the second metal surface area in step i) after said second metal surface area has been subjected to at least one scraping, brushing, grinding, etching, pickling and/or polishing step.

In some embodiments, the method further comprising, for controlling or adjusting the initial conditions for measuring the electrical resistance of cleaned metal surfaces, i) measuring, prior to step d), a third test electrical resistance value $R_{O3}$ by
  providing a first metal surface area belonging to the cleaned metal surface of the metal component of the industrial plant after step a), and optionally step b), have been completed and which has subsequently been subjected to at least one scraping, brushing, grinding, etching, pickling and/or polishing step, and
  providing a second metal surface area which second metal surface area is not exposed to the process run in the chemical plant and which does not belong to the cleaned metal surface of the metal component of the industrial plant after step a), and optionally step b), have been completed, and wherein said second metal surface area is on said metal component of the industrial plant comprising the cleaned area of the metal surface or is on a metal component which is in electrical connection with said metal component of the industrial plant comprising the cleaned area of the metal surface, and
  placing the probing tip on said first metal surface area and the counter tip on the second metal surface area, or
  placing the probing tip on said second metal surface area and the counter tip on the first metal surface area, and ii) commencing with step d) if the third test electrical resistance value $R_{O3}$ is identical to or below a predetermined threshold resistance value $R_{THRESHOLD}$, which is below the pre-determined electrical resistance value $R_{DET}$, by having the counter tip placed on said second metal surface area, or iii) subjecting the first and/or second metal surface area to at least one scraping, brushing, grinding, etching, pickling and/or polishing step if the third test electrical resistance value $R_{O3}$ is above the predetermined threshold resistance value $R_{THRESHOLD}$ and commencing with steps i) and ii).

In some embodiments, the electrical resistance $R_{A1}$ measured at at least one point of the cleaned area of the metal surface according to step d) is the highest electrical resistance $R_{A1-max}$ of the individual electrical resistances $R_{A1-ind}$ measured at said cleaned area or part thereof, or is the average electrical resistance $R_{A1-av}$ of the individual electrical resistances $R_{A1-ind}$ measured at said cleaned area or part thereof.

In some embodiments, the present disclosure provides a method for polymerizing monomers or comonomers or for thermally cleaving hydrocarbons to furnish ethylene in an industrial plant, comprising the step of cleaning a metal surface of a metal component of said industrial plant with a method as described above prior to polymerizing monomers or comonomers or thermally cleaving hydrocarbons in the industrial plant.

DETAILED DESCRIPTION OF THE INVENTION

Figure 1:
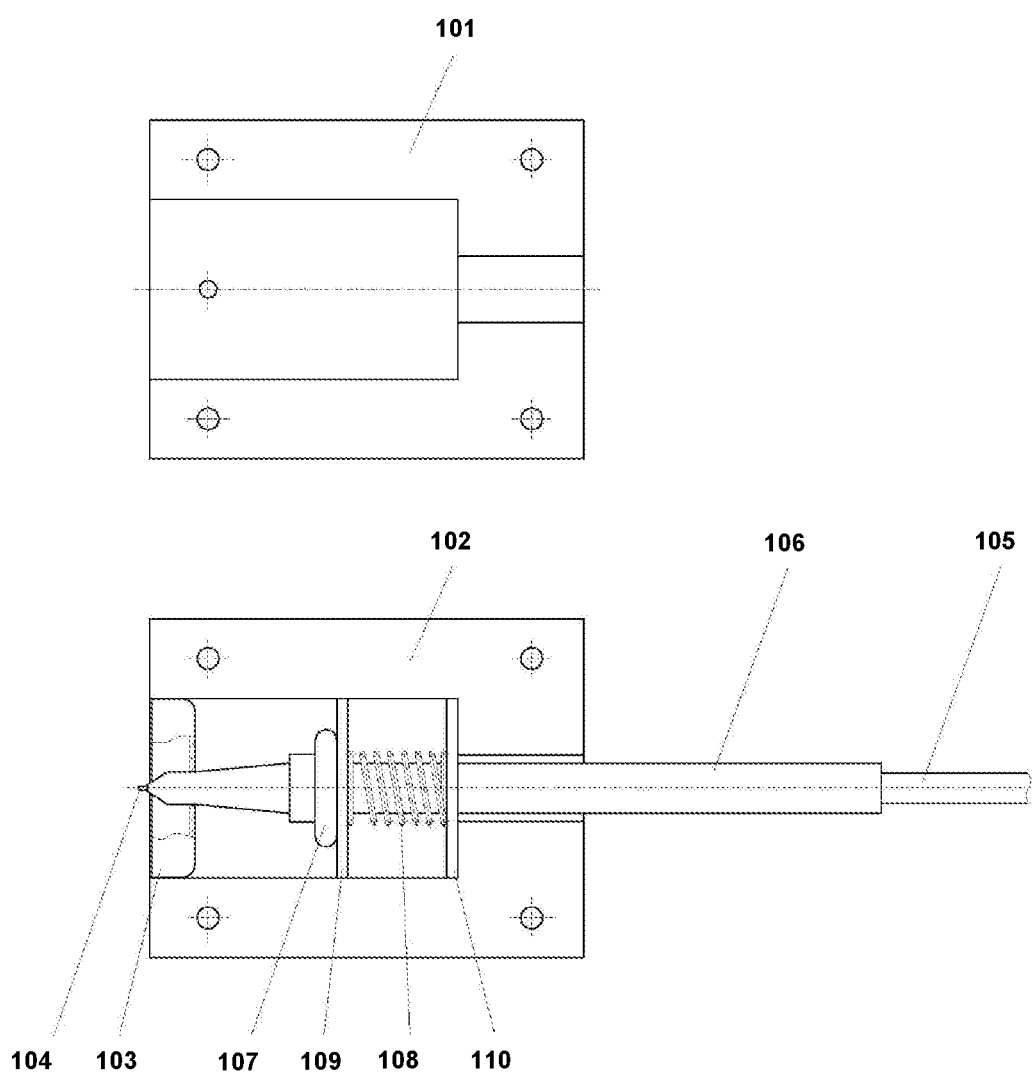
FIG. 1 shows a schematic view of a counter tip holder.

The method of the present disclosure can in one embodiment be used for cleaning metal surfaces of metal components of a chemical or petrochemical plant, such as a polyethylene or a polypropylene plan or a plant for furnishing ethylene by thermally cleaving hydrocarbons.

The present disclosure accordingly provides a method for cleaning a metal surface of a metal component of an industrial plant, comprising the steps of a) cleaning at least one area of a metal surface of a metal component after having been put into operation for an interval,
b) optionally drying the cleaned area of the metal surface of the metal component,
c) providing a pre-determined electrical resistance value $R_{DET}$ which represents an electrical resistance indicative of a sufficiently cleaned metal surface of the metal component of the industrial plant,
d) measuring the electrical resistance $R_{A1}$ of the surface of the metal component at at least one point of the cleaned area by at least one resistance meter,
e) comparing the electrical resistance $R_{A1}$ measured according to step d) with the pre-determined electrical resistance value $R_{DET}$, and
f) repeating steps a), d) and e), and optionally b), if the electrical resistance $R_{A1}$ is greater than the pre-determined electrical resistance value $R_{DET}$, or
g) terminating cleaning of the surface area of the metal component if the electrical resistance value $R_{DET}$ is smaller than or identical to the pre-determined electrical resistance value $R_{DET}$.

In some embodiments, the industrial plant is a chemical or petrochemical plant.

For cleaning operation in step a), the metal surfaces of metal components of a chemical or petrochemical plant can for example be treated with high-pressure water jets, e.g. having a water pressure in the range from 1,000 to 1,600 bar. In some cases, desalinated water can be used. In addition or alternatively, cleaning can also encompass mechanical cleaning processes such as scraping or brushing.

In some embodiments, the metal component of an industrial plant is selected from the group consisting of heat exchangers, containers, reactors, tanks, vessels, pipes, cracking furnaces, tubes, filters, valves, and of parts thereof or from moveable equipment such as silo trucks, tank wagons or parts thereof.

The measurement of the electrical resistances may occur by at least one resistance meter. Resistance meters for measuring an electrical resistance may be commercially available. Such resistance meters may have two measuring contacts for determining an electrical resistance. According to the method of the present disclosure, one of the measuring contacts is employed as a probing tip which is brought into contact with the metal surface to be examined, for example the cleaned area employed in step d) of the present method. In one embodiment the method, the probing tip is a punctual tip. In another embodiment, the probing tip is a sliding contact. Another measuring contact of the resistance meters of the present disclosure is employed as counter tip. It is possible, that two or more punctual tips or two or more sliding contacts are electrically connected and used as one measuring contact for one resistance meter, that means that two or more punctual tips or two or more sliding contacts are electrically connected and used as one probing tip or as one counter tip.

According to the method of the present disclosure, the term "measuring the electrical resistance $R_{A1}$ of the surface of the metal component" can mean that one single measurement of the electrical resistance $R_{A1}$ at one point of the cleaned area of the metal surface is carried out, for example using a punctual tip. Then this single value of the electrical resistance $R_{A1}$ is compared the pre-determined electrical resistance value $R_{DET}$. The term "measuring the electrical resistance $R_{A1}$ of the surface of the metal component" can further mean that a multitude of single measurement is carried out. The electrical resistance $R_{A1}$ is then the highest electrical resistance $R_{A1-max}$ of the individual electrical resistances $R_{A1-ind}$ measured at said cleaned area or part thereof, or is the average electrical resistance $R_{A1-av}$ of the individual electrical resistances $R_{A1-ind}$ measured at said cleaned area or part thereof. In an embodiment of the present disclosure, the term "measuring the electrical resistance $R_{A1}$ of the surface of the metal component" stands for measuring the electrical resistance $R_{A1}$ of the surface of the metal component over at least a part of the cleaned area of the metal surface along a continuous path, for example using a probing tip which is a sliding contact, i.e. a measuring contact which represents or comprises a moveable contact. The electrical resistance $R_{A1}$ is then the highest electrical resistance $R_{A1-max}$ of the individual electrical resistances $R_{A1-ind}$ measured at said cleaned area or part thereof, or is the average electrical resistance $R_{A1-av}$ of the individual electrical resistances $R_{A1-ind}$ measured at said cleaned area or part thereof.

In an embodiment of the present disclosure, two or more resistance meters are used in parallel for measuring the electrical resistance of the surface of the metal component. These two or more resistance meters may then be combined in one apparatus with one data output or the two or more resistance meters operate independently, however for example with a combined evaluation of the measuring results.

The electrical resistance according to the method of the present disclosure can be measured in the form of DC resistance or AC resistance. According to an embodiment of the method of the present disclosure, DC resistance is measured.

Metal components used for industrial plants may be well-defined both in terms of dimensions and materials. The inherent properties of the materials used for such components may therefore be known and can be counter-checked. This also includes the electrical conductivity or electrical resistance of a metal component of an industrial plant. Such inherent electrical resistance according to one embodiment can be determined and kept as the pre-determined electrical resistance value $R_{DET}$.

The electrical resistance of metal components can also be checked once having been assembled and fixed. In such a state prior to any of its intended usages and being in a condition that production can instantaneously start, i.e. prior to being put into operation for the very first time, a standardized electrical resistance $R_{S1}$ or conductivity can be determined over the metal surfaces of all metal components or part thereof which will be subjected to cleaning processes during maintenance intervals once the plant has been put into operation. Such standardized electrical resistance according to another embodiment can be determined and kept as the pre-determined electrical resistance value $R_{DET}$.

According to another embodiment, the pre-determined electrical resistance value $R_{DET}$ can be set by use of experimental test runs relating to determining the degree of cleaning. Additionally or alternatively, said pre-determined electrical resistance value $R_{DET}$ can be based on the experience of the person skilled in the art.

For example, in some cases it can be sufficient to set the pre-determined electrical resistance value $R_{DET}$ at 20, 50 or 100 Ohm; and in some other embodiments the pre-determined electrical resistance value $R_{DET}$ can be set at 200, 500 or 1000 Ohm to indicate that a sufficient degree of cleaning of an industrial plant has been obtained. In some cases, it largely depends on the reaction conducted in an industrial plant and/or the set-up of said industrial plant or of its components which degree of cleaning guarantees a reduction in maintenance cycles and/or a significant elongation of reaction periods during which high reaction efficiencies can be maintained.

Accordingly, depending on the degree of cleaning needed for a specific manufacturing process, various figures for the pre-determined electrical resistance value $R_{DET}$ can be established and used in order to decide whether a specific surface area $A_n$ of a metal component or the entire metal component of even the entire plant needs to be subjected to additional cleaning or whether a sufficient degree of cleaning has been obtained. This predetermined figure for the pre-determined electrical resistance value $R_{DET}$ can also be called target figure.

In some cases, good reproducible results are obtained by taking special care of the placement of the counter tip of the resistance meter. Here, the method of the present disclosure according to a first variant further comprises, for controlling and, if need be, adjusting the initial conditions for measuring the electrical resistance of cleaned metal surfaces, i) measuring, prior to step d), a first test electrical resistance value $R_{01}$ on a first metal surface area belonging to the cleaned metal surface of the metal component of the industrial plant after steps a), and optionally b), have been completed and after said first metal surface area of the cleaned metal surface area has subsequently been subjected to at least one scraping, brushing, grinding, etching, pickling and/or polishing step in order to bare the metal, and ii) commencing with step d) if the first test electrical resistance value $R_{01}$ is identical to or below a predetermined threshold resistance value $R_{THRESHOLD}$, which is below the pre-determined electrical resistance value $R_{DET}$, by having the counter tip placed on said first metal surface area, or iii) repeating the at least one scraping, brushing, grinding, etching, pickling and/or polishing step if the first test electrical resistance value $R_{01}$ is above the predetermined threshold resistance value $R_{THRESHOLD}$ and commencing with steps i) and ii).

According to an embodiment for measuring the electrical resistance value $R_{01}$, both measuring contacts of the resistance meter, the probing tip and the counter tip, are brought into contact with said first metal surface area.

Accordingly, the above measurement of $R_{01}$ can be used to determine or test whether said first metal surface area can be considered to represent a suitable contact area for the counter tip during measurement of the electrical resistance $R_{A1}$. For example, if the test electrical resistance measured is about 20 Ohm or below or is even about 10 Ohm or below said first metal surface area can be reliably used as a contact area for the counter tip of the resistance meter. Concomitantly, the above test measurement also provides information on whether the resistance meter is properly functioning. If with this test measurement unusually high resistance values $R_{01}$ are measured, e.g. higher than 20 Ohm or 10 Ohm as indicated above, and if this cannot be attributed to a properly bared first metal surface area the resistance meter should be subjected to a thorough testing or should be replaced.

Steps i) and ii) or steps i), ii) and iii), respectively, can for example be carried out prior to step a) or b) or, alternatively, after step a) or step b).

According to a second variant the method of the present disclosure further comprises, for controlling and, if need be, adjusting the initial conditions for measuring the electrical resistance of cleaned metal surfaces,
i) measuring, prior to step d), a second test electrical resistance value $R_{02}$ on a second metal surface area, wherein said second metal surface area is not exposed to the process run in the chemical plant and which does not belong to the cleaned metal surface of the metal component of the industrial plant, and wherein said second metal surface area is either on said metal component of the industrial plant comprising the cleaned area of the metal surface or is on a metal component which is in electrical connection with said metal component of the industrial plant comprising the cleaned area of the metal surface,
ii) commencing with step d) if the second test electrical resistance value $R_{02}$ is identical to or below a predetermined threshold resistance value $R_{THRESHOLD}$, which is below the pre-determined electrical resistance value $R_{DET}$, by having the counter tip placed on said second metal surface area, or
iii) subjecting the second metal surface area to at least one scraping, brushing, grinding, etching, pickling and/or polishing step if the second test electrical resistance value $R_{02}$ is above the predetermined threshold resistance value $R_{THRESHOLD}$ and commencing with steps i) and ii).

In an embodiment, the test electrical resistance value $R_{02}$ is measured on the second metal surface area after said second metal surface area has been subjected to at least one scraping, brushing, grinding, etching, pickling and/or polishing step.

According to an embodiment for measuring the electrical resistance value $R_{02}$, both measuring contacts of the resistance meter, the probing tip and the counter tip, are brought into contact with said second metal surface area.

Again, the above measurement of $R_{02}$ can be used to determine or test whether said second metal surface area can be considered to represent a suitable contact area for the counter tip during measurement of the electrical resistance $R_{A1}$. For example, if the test electrical resistance measured is about 20 Ohm or below or is even about 10 Ohm or below said second metal surface area can be reliably used as a contact area for the counter tip of the resistance meter. Concomitantly, also the above test measurement also provides information on whether the resistance meter is properly functioning. If with this test measurement unusually high resistance values $R_{02}$ are measured, e.g. higher than 20 Ohm or 10 Ohm as indicated above, and if this cannot be attributed to a properly bared second metal surface area the resistance meter should be subjected to a thorough testing or should be replaced.

Again, steps i) and ii) or steps i), ii) and iii), respectively, can for example be carried out prior to step a) or b) or, alternatively, after step a) or step b).

According to a third variant the method of the present disclosure further comprises, for controlling and, if need be, adjusting the initial conditions for measuring the electrical resistance of cleaned metal surfaces,
i) measuring, prior to step d), a third test electrical resistance value $R_{03}$ by
   providing a first metal surface area belonging to the cleaned metal surface of the metal component of the industrial plant after step a), and optionally step b), have been completed and which has subsequently been subjected to at least one scraping, brushing, grinding, etching, pickling and/or polishing step, and
   providing a second metal surface area which second metal surface area is not exposed to the process run in the chemical plant and which does not belong to the cleaned metal surface of the metal component of the industrial plant after step a), and optionally step b), have been completed, and wherein said second metal surface area is on said metal component of the industrial plant comprising the cleaned area of the metal surface or is on a metal component which is in electrical connection with said metal component of the industrial plant comprising the cleaned area of the metal surface, and
   placing the probing tip on said first metal surface area and the counter tip on the second metal surface area, or
   placing the probing tip on said second metal surface area and the counter tip on the first metal surface area, and
ii) commencing with step d) if the third test electrical resistance value $R_{03}$ is identical to or below a predetermined threshold resistance value $R_{THRESHOLD}$, which is below the pre-determined electrical resistance value $R_{DET}$, by having the counter tip placed on said second metal surface area, or
iii) subjecting the first and/or second metal surface area to at least one scraping, brushing, grinding, etching, pickling and/or polishing step if the third test electrical resistance value $R_{03}$ is above the predetermined threshold resistance value $R_{THRESHOLD}$ and commencing with steps i) and ii).

Alternatively, the probing tip can be placed on said second metal surface area and the counter tip on the first metal surface area. In one embodiment said second metal surface area has been subjected to at least one scraping, brushing, grinding, etching, pickling and/or polishing step prior to placing a measuring contact thereon.

Again, the above measurement of $R_{03}$ can be used to determine or test whether said first and second metal surface areas can be considered to represent suitable contact areas for the sliding contact and/or the counter tip during measurement of the electrical resistance $R_{A1}$. For example, if the test electrical resistance measured is about 20 Ohm or below or is even about 10 Ohm or below said first and/or second metal surface areas can be reliably used as a contact area for the sliding contact and the counter tip of the resistance meter. Concomitantly, also the above test measurement also provides information on whether the resistance meter is properly functioning. If with this test measurement unusually high resistance values $R_{03}$ are measured, e.g. higher than 20 Ohm or 10 Ohm as indicated above, and if this cannot be attributed to a properly bared first and/or second metal surface area the resistance meter should be subjected to a thorough testing or should be replaced.

Again, steps i) and ii) or steps i), ii) and iii), respectively, can for example be carried out prior to step a) or b) or, alternatively, after step a) or step b).

According to another embodiment of the present disclosure for controlling or adjusting the initial conditions for measuring the electrical resistance of cleaned metal surfaces it is also possible to carry out both the aforementioned first and second variant or the aforementioned first and third variant or the aforementioned second and third variant or to carry out the aforementioned first, second and third variant in order to obtain and even more reliable initial setup for conducting the electrical resistance measurements.

Scraping, brushing, grinding, etching, pickling and/or polishing may exposes the naked metal and yields a metal surface having a metallic gloss. Such mechanical treatment means to obtain a sufficiently clean and bare metal area without non-metallic layer materials thereon encompasses for example treating the metal surface with sand or abrasive paper and/or steel or corundum brushes. In these first and second metal surface areas it is the metal as such, that is the neat metal without non-metal residues as obtained by scraping, brushing, grinding, etching, pickling and/or polishing, for example by scraping and brushing, scraping or grinding or by scraping and polishing or grinding and polishing or brushing and polishing or by scraping and etching or polishing and etching or by polishing and pickling or scrapping and pickling or grinding and etching or grinding and pickling, which is subjected to the determination of the electrical resistance value $R_{01}$, $R_{02}$ and $R_{03}$, respectively.

If the cleaned area by nature of the cleaning process is still wet and if the standardized electrical resistance has been measured for the metal surface of the metal component under scrutiny under dry conditions, said cleaned area should be dried prior to any measurements of its electrical properties.

In an embodiment of the present disclosure, the measuring of the electrical resistances occurs by a resistance meter which comprises at least one sliding contact, in particular two or more sliding contacts, wherein the at least one sliding contact represents the probing tip, and another contact is the counter tip. According to an embodiment, the counter tip is placed on said first metal surface area or on said second metal surface area.

In a pragmatic embodiment, the electrical resistance $R_{A1}$ of the metal component cleaned according to step a), and optionally step b), is measured in step d) by moving the probing tip over at least part of the cleaned area of the metal surface and having placed the counter tip on a metal surface area belonging to the cleaned metal surface of the metal component of the industrial plant after step a), and optionally step b), have been completed and after said metal surface area of the cleaned metal surface area has subsequently been subjected to at least one scraping, brushing, grinding, etching, pickling and/or polishing step or having placed the counter tip on a metal surface area wherein said metal surface area is not exposed to the process run in the chemical plant and which does not belong to the cleaned metal surface of the metal component of the industrial plant after step a), and optionally step b), have been completed, and wherein said metal surface area is either on said metal component of the industrial plant comprising the cleaned area of the metal surface or is on a metal component which is in electrical connection with said metal component of the industrial plant comprising the cleaned area of the metal surface.

Accordingly, in one embodiment, the counter tip is placed on a (second) metal surface area of said metal component of the industrial plant comprising the cleaned area of the metal surface which (second) metal surface area is not exposed to the process run in the chemical plant and thus does not need to be subjected to cleaning step a). Alternatively, said (second) metal surface area can also be located on a metal component being in electrical connection with said metal component of the industrial plant comprising the cleaned area of the metal surface. According to an exemplary mode of action, said (second) metal surface area has been subjected to at least one scraping, brushing, grinding, etching, pickling and/or polishing step before said counter tip is brought in contact therewith and the measurement is conducted. Said (second) metal surface area can for example be on the outside of the component, such as the outside of a tube or pipe or on the outer wall of a vessel.

For both the first and the second metal surface area it may be sufficient to cover a surface area in the range from about 1 cm$^2$ to 4 cm$^2$, e.g. 2 cm$^2$.

For the general setup, resistance meters can be used which are customary in the trade.

From the foregoing it can be derived that, in the meaning of the present disclosure, an resistance meter and the general setup of the cleaning test can according to one embodiment be considered to be sufficiently functional if upon having conducted resistance measurements when both the probing tip and the counter tip of the resistance meter are in contact with the second metal surface area, an electrical resistance equal or smaller than 20 Ohm, or equal or smaller than 10 Ohm is measured.

In order to obtain reliable results respective measurements can also be applied to the first metal surface area before starting the actual measurement of the degree of cleanliness of the cleaned metal surface area of the metal component. It has been found to be pragmatic that the first metal surface area is remote from said second metal surface area. For this measurement, the contact tip should be in contact with the first metal surface area while the counter tip is in contact with the second metal surface area. If the electrical resistance measured with the said setup is at or below a certain pre-determined value, for example 20 or 10 Ohm, the electrical resistance measurement of the cleaned metal surfaces of the metal component, for example the inner wall of a tubing, can be started.

In step d), the electrical resistance $R_{A1}$ of the metal component can be measured over a continuous path or can be measured intermittently at the cleaned area of the metal surface, that is, for example, at pre-defined intervals. Measuring the electrical resistance over a continuous path may furnish good and reliable cleaning results.

According to one embodiment, the electrical resistance $R_{A1}$ measured at at least one point of the cleaned area of the metal surface according to step d) is considered to be the highest electrical resistance $R_{A1-max}$ of the individual electrical resistances $R_{A1-ind}$ measured at said cleaned area or part thereof. According to an alternative embodiment, the electrical resistance $R_{A1}$ measured at least one point of the cleaned area of the metal surface according to step d) is considered to be the average electrical resistance $R_{A1-av}$ of the individual electrical resistances $R_{A1-ind}$ measured at said cleaned area or part thereof.

In an embodiment of the present disclosure, the counter tip is a punctual tip held by a magnet to a surface of the metal component of the industrial plant or to a surface of a metal part in electrical connection with the metal component of the industrial plant. In this embodiment, the counter tip can be fast and easily connected to the metal surface in a reliable manner but provides full flexibility in selecting the position for the counter tip. In this embodiment, the counter tip may be movably installed within a counter tip holder comprising a magnet and a compression spring. The compression spring provides for a defined static force which may be vertically transferred to the metal surface via the conductive measuring tip. This improves the quality of the measurement and prevents handling errors.

The body of the counter tip holder may be made of a conductive material, such as a metal, and the body of the counter tip holder is in electrical connection with the metal surface when the counter tip holder is attached to the metal surface. This allows for a simple possibility for controlling and, if need be, adjusting the placement of the counter tip of the resistance meter, i.e. allows for a simple possibility to ensure that the first test electrical resistance value $R_{01}$ is identical to or below a predetermined threshold resistance value $R_{THRESHOLD}$, because it is then sufficient that the probing tip is brought into contact with the body of the counter tip holder to measure the electrical resistance value $R_{01}$.

FIG. 1 shows a schematic view of a counter tip holder according to an embodiment of the present disclosure. The counter tip holder comprises a first half of a body 101 and a second first half of a body 102 which can be firmly connected together and which form, when being connected, a body having a cylindrical cavity. The outer end of the cavity is closed by a disc-shaped magnet 103 having a hole in the middle. The counter tip, which is movably installed within the counter tip holder, comprises a conductive measuring tip 104, which is electrically connected to a cable 105. The counter tip further comprises a polymeric insulation 106, which forms a border 107 at the side of the measuring tip. The counter tip holder further comprises, within the cavity, a spring 108, which is placed around the insulation 106 and situated between a front guide washer 109 and a back guide washer 110. A counter tip holder as shown in FIG. 1 provides the possibility to reliably connect a counter tip to a metal surface, however in a very easy and flexible manner.

In an embodiment of the present disclosure, the metal surface to be cleaned is the inner surface of a tube in a heat exchanger and the measuring of the electrical resistances occurs by a resistance meter comprising at least one sliding contact as probing tip and another contact as counter tip, and the at least one sliding contact can be moved to all positions of the inner surface of the tube.

According to another aspect of the present disclosure, a method for polymerizing monomers or comonomers or for thermally cleaving hydrocarbons to furnish ethylene in an industrial plant is provided, comprising the step of cleaning a metal surface of a metal component of said industrial plant by use of the method of the present disclosure as outlined above prior to polymerizing monomers or comonomers or prior to thermally cleaving hydrocarbons in the industrial plant. The industrial plant for thermally cleaving hydrocarbons to furnish ethylene may comprise a cracking furnace comprising cracking tubes or coils. With a cracking furnace designed and arranged to furnish ethylene regularly also gaseous side products are produced, such as hydrogen, propylene, butene or butadiene, as well as some non-gaseous side products. By employing the method of the present disclosure for cleaning the metal surface of a metal component of an industrial plant, in particular of the cracking tubes or coils of such cracking furnace, before conducting the respective reaction or process product yields can be increased and the frequency of maintenance intervals can be significantly reduced.

With the process of the present disclosure it is possible to determine electrical resistance over a wide range of predefined surface areas. For all these predefined surface areas $A_n$, it can be determined whether the measured electrical resistance $R_{An}$ is greater, smaller or equal to the pre-determined electrical resistance value $R_{DET}$ and thus decided whether the target figure has been met.

When applying the method of the present disclosure it was found that considerably longer operating times of metal components of industrial plants can be accomplished leading to a reduction of the maintenance costs. This applies, in particular to heat exchangers as used, for example, in plants for the manufacture of polyethylene. However, effects in terms of prolonged operation times can also be accomplished with respect to, for example containers, reactors, tanks, vessels, pipes, filters, silo trucks, tank wagons etc.

In general, with the method of the present disclosure, for example, in connection with the production of polyethylene, improved performance in heat transfer, decreased temperature for flow, minimized pressure losses, higher streaming volume and/or reduced risk of interruption of operations or leaking can be obtained. This has the overall effect of lower production costs and reduced maintenance expenditures.

With the method of the present disclosure it is also possible to reduce the workload and time and thereby also the costs for assessing the cleaning progress during cleaning operations of chemical or petrochemical plants by using a defined surface area of the metal surface of a metal component of step a) as a reference surface. Accordingly, one or more defined surface areas can be selected from the at least one area of the metal surface of the metal component having been cleaned according to step a), and optionally dried according to step b), and wherein solely said one or more defined surface areas are then subjected to process steps d) and e). Hence, in this embodiment, it is said defined surface area which is selected from the at least one area(s) of the metal surface of the metal component having been cleaned according to step a), and optionally dried according to step b), and it is this defined surface area(s) which here is solely subjected to process steps d) and e).

In other words, the method of the present disclosure allows to select a specific defined surface of a metal component which needs cleaning, and, furthermore to confine the assessment of the cleaning status of the industrial plant to be cleaned to this specific surface even though the entire plant has been subjected to cleaning. In the latter case, only the reference surface is subjected to process steps c) to g) and optionally to process step b). In one embodiment, it is recommendable to select a surface as the reference surface, i.e. defined surface area, which needs the highest cleaning effort to arrive at a satisfactory cleaning result. If this defined surface area suffices the needs of process step g), the cleaning of the entire plant can be terminated. With the method of the present disclosure it is possible to reliably determine in a very efficient manner when an industrial plant, in particular a chemical or petrochemical plant, for example a steam cracker or a polyethylene plant, can be started again after cleaning even though not all of its components have been assessed as to their cleaning status.

Figure 2:
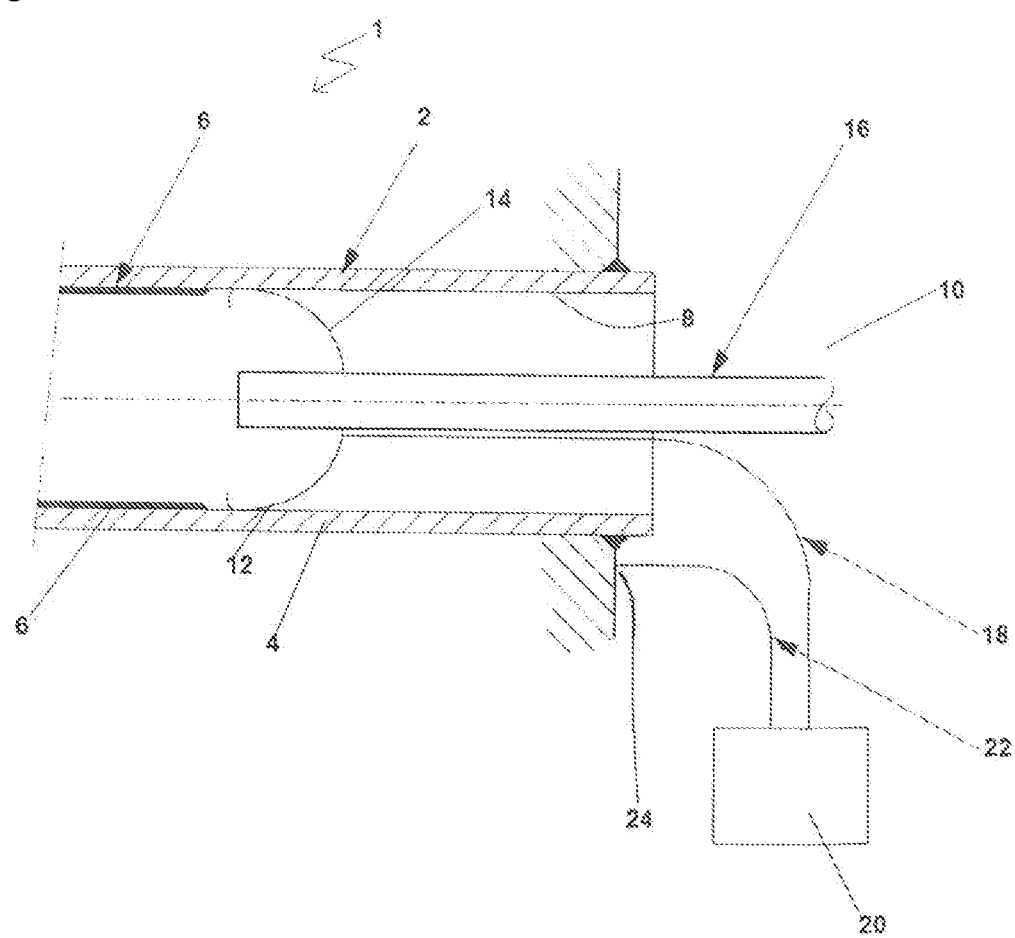
FIG. 2 shows a schematic view of the method of determining the electrical resistance in a metal component of an industrial plant.

FIG. 2 shows a schematic cross-sectional view of a metal component 1 of an industrial plant comprising a metal pipe 2. The inner wall 4 of the metal pipe 2 is still containing some caking residues 6 while further parts 8 of the inner wall 4 are completely clean. Further, a resistance meter 10 is shown comprising sliding contacts 12 and 14 which due to their inherent spring force are pressed against the inner wall 4 and which are attached to a guiding bar 16. The sliding contacts 12, 14 are electrically connected by wire 18 to a detecting and analyzing device 20 which is also connected to the metal pipe 2 via wire 22 leading to counter tip 24. Depending on whether the sliding contacts 12, 14 are in contact with either the clean metal surface 8 or the surface of the inner wall still comprising caking layers 6 different electrical resistance values are measured. While at the sufficiently clean metal surface 8 the electrical resistance $R_{A1}$ will be equal to or below a pre-determined electrical resistance value $R_{DET}$, the resistance $R_{A1}$ will be higher than the pre-determined electrical resistance value $R_{DET}$ where caking 6 is still present. In this manner it can be easily determined whether the metal surface of a component of an industrial plant is sufficiently clean.

With the present disclosure the cleanliness can also reliably be checked at inaccessible or not visible locations, such as the interior walls of containers, equipment, or pipes. With the method of the present disclosure the desired degree of cleanliness of metal surfaces of metal components can be safeguarded in a quick and reliable manner.

While multiple embodiments are disclosed, still other embodiments will become apparent to those skilled in the art from the detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

What is claimed is:

1. A method for cleaning a metal surface of a metal component of an industrial plant, comprising the steps of
   a) cleaning at least one area of a metal surface of a metal component after having been put into operation for an interval,
   b) optionally drying the at least one cleaned area of the metal surface of the metal component
   c) providing a pre-determined electrical resistance value $R_{DET}$ which represents an electrical resistance indicative of a sufficiently cleaned metal surface of the metal component of the industrial plant,
   d) measuring the electrical resistance $R_{A1}$ of the metal surface of the metal component at at least one point of the at least one cleaned area by at least one resistance meter,
   e) comparing the electrical resistance $R_{A1}$ measured according to step d) with the pre-determined electrical resistance value $R_{DET}$, and
   f) repeating steps a), d) and e) if the electrical resistance $R_{A1}$ is greater than the pre-determined electrical resistance value $R_{DET}$, or
   g) terminating cleaning of the at least one area of the metal surface of the metal component if the electrical resistance value $R_{A1}$ is smaller than or identical to the pre-determined electrical resistance value $R_{DET}$,
wherein the electrical resistance $R_{A1}$ of the metal component cleaned according to step a), and optionally step b), is measured in step d) by moving a probing tip over at least part of the cleaned area of the metal surface, and having placed a counter tip on a metal surface area belonging to the cleaned metal surface of the metal component of the industrial plant after step a), and optionally step b), have been completed and after said metal surface area of the cleaned metal surface area has subsequently been subjected to at least one scraping, brushing, grinding, etching, pickling and/or polishing step, or having placed a counter tip on a metal surface area, wherein said metal surface area is not exposed to a process run in the industrial plant and which does not belong to the cleaned metal surface of the metal component of the industrial plant after step a), and optionally step b), have been completed, and wherein said metal surface area is on said metal component of the industrial plant comprising the cleaned area of the metal surface or is on a metal component which is in electrical connection with said metal component of the industrial plant comprising the cleaned area of the metal surface wherein said metal surface area which is not exposed to the process run in the industrial plant and which does not belong to the cleaned metal surface of the metal component of the industrial plant after step a), and optionally step b), have been completed, is subjected to at least one scraping, brushing, grinding, etching, pickling and/or polishing step before the counter tip is brought in contact therewith.

2. The method of claim 1, comprising repeating step f) the steps a), b), d) and e) if the electrical resistance $R_{A1}$ is greater than the pre-determined electrical resistance value $R_{DET}$.

3. The method of claim 1, wherein the metal component is a heat exchanger, container, reactor, tank, vessel, pipe, cracking furnace, tube, filter, silo truck, tank wagon or a part thereof.

4. The method of claim 1, wherein the industrial plant is a chemical or petrochemical plant.

5. The method of claim 1, wherein the measuring of the electrical resistances occurs by a resistance meter comprising at least one probing tip and another contact, which is a counter tip, and the counter tip is a punctual tip held by a magnet to a surface of the metal component of the industrial plant or to a surface of a metal part in electrical connection with the metal component of the industrial plant.

6. The method of claim 5, wherein the counter tip is movably installed within a counter tip holder comprising a magnet and a compression spring.

7. The method of claim 1, wherein the measuring of the electrical resistances occurs by a resistance meter comprising at least one sliding contact, wherein the at least one sliding contact represents the probing tip, and another contact is the counter tip.

8. The method of claim 1, wherein the metal surface is the inner surface of a tube in a heat exchanger and the measuring of the electrical resistances occurs by a resistance meter comprising at least one sliding contact as probing tip and another contact as counter tip, and the at least one sliding contact can be moved to all positions of the inner surface of the tube.

9. The method of claim 1, wherein one or more defined surface areas are selected from the at least one area of the metal surface of the metal component having been cleaned according to step a), and optionally dried according to step b), and solely said one or more defined surface areas are subjected to process steps d) and e).

10. The method of claim 1, wherein the cleaning of the metal surface of the metal component of the industrial plant or of a metal component thereof is terminated as soon as the at least one areas meets the requirement of process step g).

11. The method of claim 1, wherein, in step d), the electrical resistance $R_{A1}$ of the metal component is measured along a continuous path or intermittently at the cleaned area of the metal surface.

12. The method of claim 1, further comprising, for controlling or adjusting an initial condition for measuring the electrical resistance of cleaned metal surfaces,
   i) measuring, prior to step d), a first test electrical resistance value $R_{01}$ on a first metal surface area belonging to the cleaned metal surface of the metal component of the industrial plant after steps a), and optionally b), have been completed and after said first metal surface area of the cleaned metal surface area has subsequently been subjected to at least one scraping, brushing, grinding, etching, pickling and/or polishing step in order to bare the metal, and
   ii) commencing with step d) if the first test electrical resistance value $R_{01}$ is identical to or below a pre-determined threshold resistance value $R_{THRESHOLD}$, which is below the pre-determined electrical resistance value $R_{DET}$, by having the counter tip placed on said first metal surface area, or
   iii) repeating the at least one scraping, brushing, grinding, etching, pickling and/or polishing step if the first test electrical resistance value $R_{01}$ is above the predetermined threshold resistance value $R_{THRESHOLD}$ and commencing with steps i) and ii).

13. The method of claim 1, wherein step d) is performed multiple times and the electrical resistance $R_{A1}$ measure at at least one point of the cleaned area of the metal surface according to step d) is the highest electrical resistance $R_{A1-max}$ of the individual electrical resistances $R_{A1-ind}$ measured at said cleaned area or part thereof, or is the average electrical resistance $R_{A1-av}$ of the individual electrical resistances $R_{A1-ind}$ measured at said cleaned area or part thereof.

14. The method of claim 1 comprising the step of polymerizing monomers or comonomers or thermally cleaving hydrocarbons to furnish ethylene in an industrial plant, wherein the step of cleaning a metal surface of a metal component of said industrial plant is performed prior to polymerizing monomers or comonomers or thermally cleaving hydrocarbons in the industrial plant.

15. A method for cleaning a metal surface of a metal component of an industrial plant, comprising the steps of
   a) cleaning at least one area of a metal surface of a metal component after having been put into operation for an interval,
   c) providing a pre-determined electrical resistance value $R_{DET}$ which represents an electrical resistance indicative of a sufficiently cleaned metal surface of the metal component of the industrial plant,
   d) measuring the electrical resistance $R_{A1}$ of the metal surface of the metal component at at least one point of the at least one cleaned area by at least one resistance meter,
   e) comparing the electrical resistance $R_{A1}$ measured according to step d) with the pre- determined electrical resistance value $R_{DET}$, and
   f) repeating steps a), d) and e) if the electrical resistance $R_{A1}$ is greater than the pre-determined electrical resistance value $R_{DET}$, or
   g) terminating cleaning of the at least one area of the metal surface of the metal component if the electrical resistance value $R_{A1}$ is smaller than or identical to the pre-determined electrical resistance value $R_{DET}$,
controlling or adjusting an initial condition for measuring the electrical resistance of cleaned metal surfaces,
   i) measuring, prior to step d), a second test electrical resistance value $R_{02}$ on a second metal surface area, wherein said second metal surface area is not exposed to a process run in the industrial plant and which does not belong to the cleaned metal surface of the metal component of the industrial plant, and wherein said second metal surface area is either on said metal component of the industrial plant comprising the cleaned area of the metal surface or is on a metal component which is in electrical connection with said metal component of the industrial plant comprising the cleaned area of the metal surface,
   ii) commencing with step d) if the second test electrical resistance value $R_{02}$ is identical to or below a predetermined threshold resistance value $R_{THRESHOLD}$, which is below the pre-determined electrical resistance value $R_{DET}$, by having the counter tip placed on said second metal surface area, or
   iii) subjecting the second metal surface area to at least one scraping, brushing, grinding, etching, pickling and/or polishing step if the second test electrical resistance value $R_{02}$ is above the predetermined threshold resistance value $R_{THRESHOLD}$ and commencing with steps i) and ii).

16. The method of claim 15, wherein the second test electrical resistance value $R_{02}$ is measured on the second metal surface area in step i) after said second metal surface area has been subjected to at least one scraping, brushing, grinding, etching, pickling and/or polishing step.

17. The method of claim 15 comprising the step of polymerizing monomers or comonomers or thermally cleaving hydrocarbons to furnish ethylene in an industrial plant, wherein the step of cleaning a metal surface of a metal component of said industrial plant is performed prior to polymerizing monomers or comonomers or thermally cleaving hydrocarbons in the industrial plant.

18. A method for cleaning a metal surface of a metal component of an industrial plant, comprising the steps of
   a) cleaning at least one area of a metal surface of a metal component after having been put into operation for an interval,
   b) optionally drying the at least one cleaned area of the metal surface of the metal component,
   c) providing a pre-determined electrical resistance value $R_{DET}$ which represents an electrical resistance indicative of a sufficiently cleaned metal surface of the metal component of the industrial plant,
   d) measuring the electrical resistance $R_{A1}$ of the metal surface of the metal component at at least one point of the at least one cleaned area by at least one resistance meter,
   e) comparing the electrical resistance $R_{A1}$ measured according to step d) with the pre-determined electrical resistance value $R_{DET}$, and
   f) repeating steps a), d) and e) if the electrical resistance $R_{A1}$ is greater than the pre-determined electrical resistance value $R_{DTT}$, or
   g) terminating cleaning of the at least one area of the metal surface of the metal component if the electrical resistance value $R_{A1}$ is smaller than or identical to the pre-determined electrical resistance value $R_{DET}$,
controlling or adjusting an initial condition for measuring the electrical resistance of cleaned metal surfaces,
   i) measuring, prior to step d), a third test electrical resistance value $R_{03}$ by providing a first metal surface area belonging to the cleaned metal surface of the metal component of the industrial plant after step a), and optionally step b), have been completed and which has subsequently been subjected to at least one scraping, brushing, grinding, etching, pickling and/or polishing step, and providing a second metal surface area which second metal surface area is not exposed to a process run in the industrial plant and which does not belong to the cleaned metal surface of the metal component of the industrial plant after step a), and optionally step b), have been completed, and wherein said second metal surface area is on said metal component of the industrial plant comprising the cleaned area of the metal surface or is on a metal component which is in electrical connection with said metal component of the industrial plant comprising the cleaned area of the metal surface, and placing a probing tip on said first metal surface area and a counter tip on the second metal surface area, or placing a probing tip on said second metal surface area and a counter tip on the first metal surface area, and ii) commencing with step d) if the third test electrical resistance value $R_{O3}$ is identical to or below a predetermined threshold resistance value $R_{THRESHOLD}$, which is below the pre-determined electrical resistance value $R_{DET}$, by having the counter tip placed on said second metal surface area, or iii) subjecting the first and/or second metal surface area to at least one scraping, brushing, grinding, etching, pickling and/or polishing step if the third test electrical resistance value $R_{O3}$ is above the predetermined threshold resistance value $R_{THRESHOLD}$ and commencing with steps i) and ii).

* * * * *

UNITED STATES PATENT AND TRADEMARK OFFICE
CERTIFICATE OF CORRECTION

PATENT NO. : 10,702,896 B2
APPLICATION NO. : 15/868701
DATED : July 7, 2020
INVENTOR(S) : Ling Page 1 of 1

It is certified that error appears in the above-identified patent and that said Letters Patent is hereby corrected as shown below:

On the Title Page

Column 1, Item (30), Line 1, delete "17152743" and insert -- 17152743.5 --, therefor In the Specification In Column 4, Line 67, delete "Roe" and insert -- $R_{02}$ --, therefor In Column 8, Line 20, delete "$R_{DET}$can" and insert -- $R_{DET}$ can --, therefor In Column 8, Line 23, delete "$R_{DET}$can" and insert -- $R_{DET}$ can --, therefor In Column 8, Line 26, delete "$R_{DET}$at" and insert -- $R_{DET}$ at --, therefor In Column 8, Line 28, delete "$R_{DET}$can" and insert -- $R_{DET}$ can --, therefor In Column 8, Line 39, delete "$R_{DET}$can" and insert -- $R_{DET}$ can --, therefor In Column 8, Line 45, delete "$R_{DET}$can" and insert -- $R_{DET}$ can --, therefor In the Claims In Column 18, Claim 18, Line 59, after "$R_{DTT}$" insert -- $R_{DET}$ --, therefor Signed and Sealed this
Third Day of January, 2023

*Katherine Kelly Vidal*

Katherine Kelly Vidal
*Director of the United States Patent and Trademark Office*